United States Patent [19]

Taheri

[11] Patent Number: 5,112,347
[45] Date of Patent: May 12, 1992

[54] EMBOLECTOMY CATHETER, AND METHOD OF OPERATING SAME

[76] Inventor: Syde A. Taheri, 268 Dan Troy, Williamsville, N.Y. 14221

[21] Appl. No.: 699,664

[22] Filed: May 14, 1991

[51] Int. Cl.$^5$ .............................................. A61B 17/00
[52] U.S. Cl. .................................... 606/200; 606/159; 604/96; 604/106; 604/53
[58] Field of Search ................ 606/159, 167, 170–171, 606/191, 198, 200, 194; 604/96–98, 103–107, 281, 53

[56] References Cited

U.S. PATENT DOCUMENTS

| 2,854,983 | 10/1958 | Boskin | 604/105 X |
| 3,540,431 | 11/1970 | Mobin-Uddin | 606/200 X |
| 3,807,408 | 4/1974 | Summers | 604/104 |
| 3,952,747 | 4/1976 | Kimmell, Jr. | 606/200 X |
| 4,921,478 | 5/1990 | Solano et al. | 604/53 |
| 4,943,297 | 7/1990 | Savelieu et al. | 606/200 |
| 5,041,093 | 8/1991 | Chu | 604/104 |
| 5,053,008 | 10/1991 | Bajaj | 604/104 |
| 5,061,240 | 10/1991 | Cherian | 604/96 |
| 5,073,166 | 12/1991 | Parks et al. | 604/93 |

FOREIGN PATENT DOCUMENTS 240945  4/1969  U.S.S.R. .............. 604/104

*Primary Examiner*—C. Fred Rosenbaum
*Assistant Examiner*—C. Maglione
*Attorney, Agent, or Firm*—Sommer, Oliverio & Sommer

[57] ABSTRACT

An inflatable balloon-type catheter (20) for use in performing an embolectomy, includes an elongated catheter (21) having a distal end (22) adapted to be inserted through an incision into a patient's blood vessel (V). A plurality of fingers (24) having first ends (25) are mounted on the distal marginal end portion of the catheter in circumferentially-spaced relation to one another. Each of the fingers has a second end (26) arranged farther from the catheter distal end than the finger first ends. Each of the fingers is configured as a leaf-spring and has an unbiased radius of curvature such that the finger second ends are normally spaced farther radially outwardly than the finger first ends. A balloon (28) surrounds the fingers and is operatively secured to the catheter so that the fingers are arranged with an inflatable chamber (29) defined between the catheter and the balloon. A syringe or squeeze bulb (30) is arranged to selectively vary the absolute pressure within the chamber so as to selectively inflate and deflate the balloon. When inflated, the balloon forms a cup-shaped recess arranged to face the embolism, and to capture portions of the severed embolism (E). In use, the improved apparatus provides a novel method of performing an embolectomy.

16 Claims, 4 Drawing Sheets

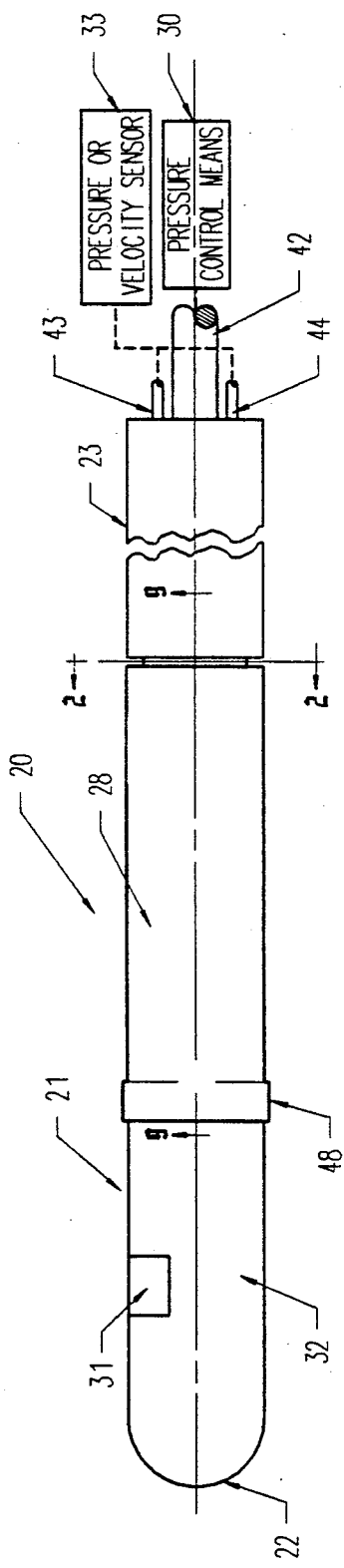
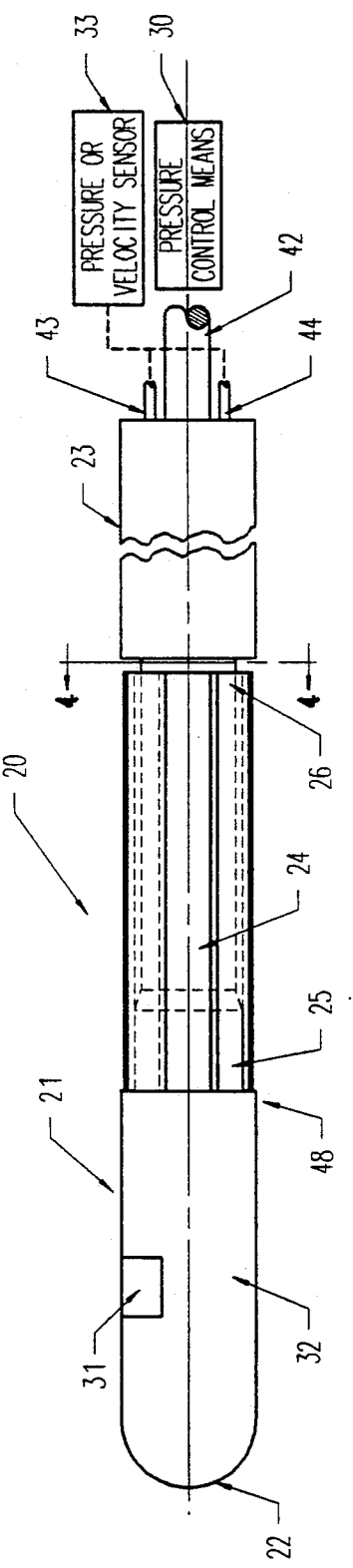
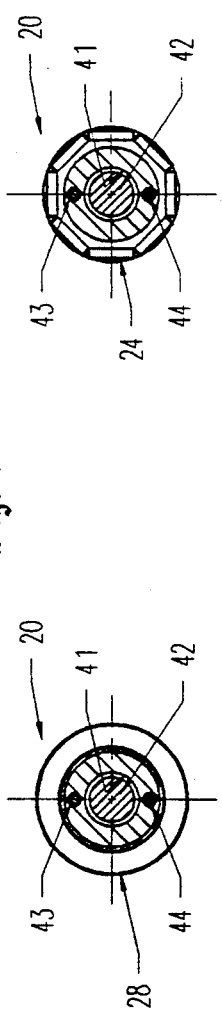
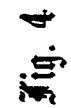

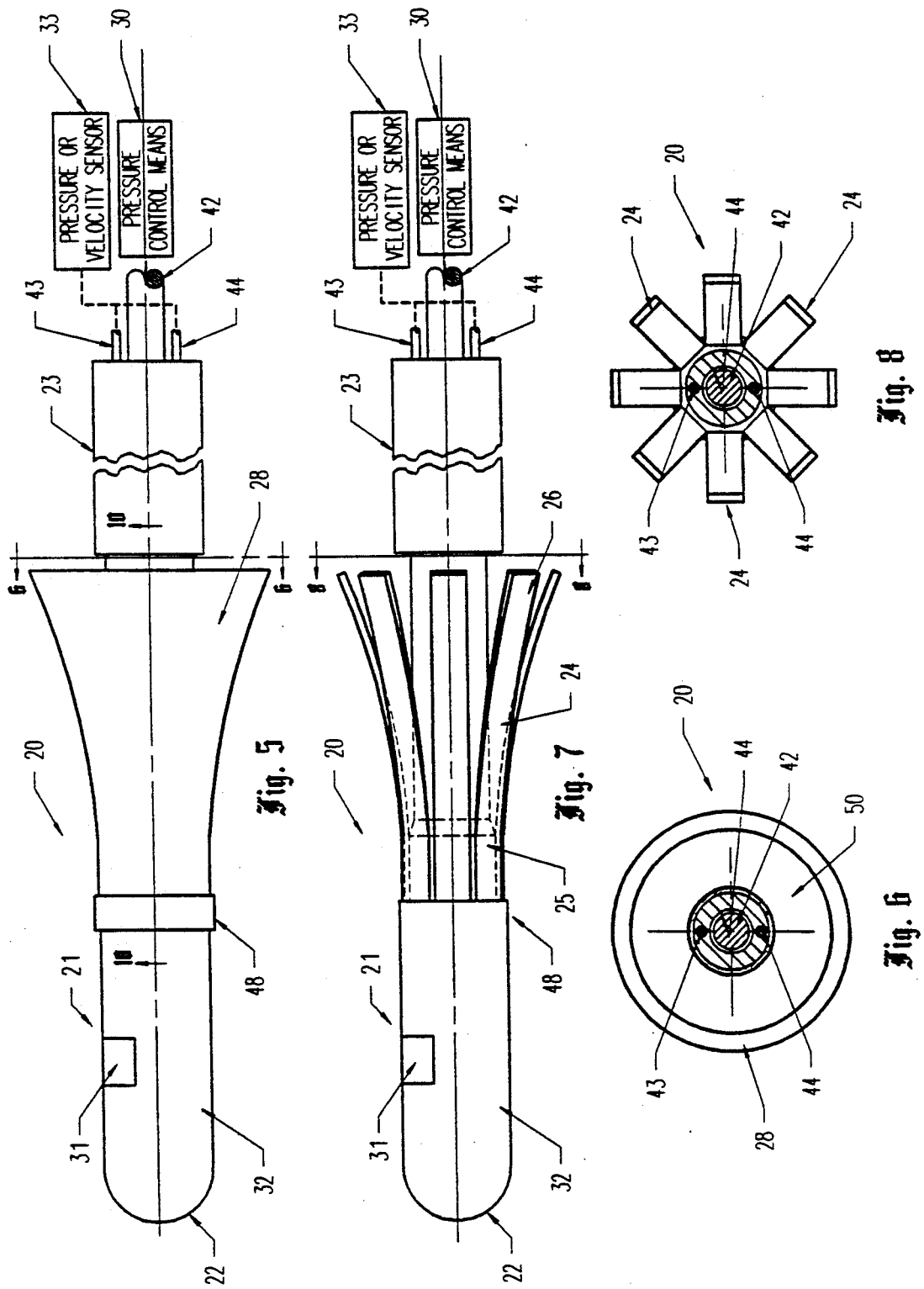

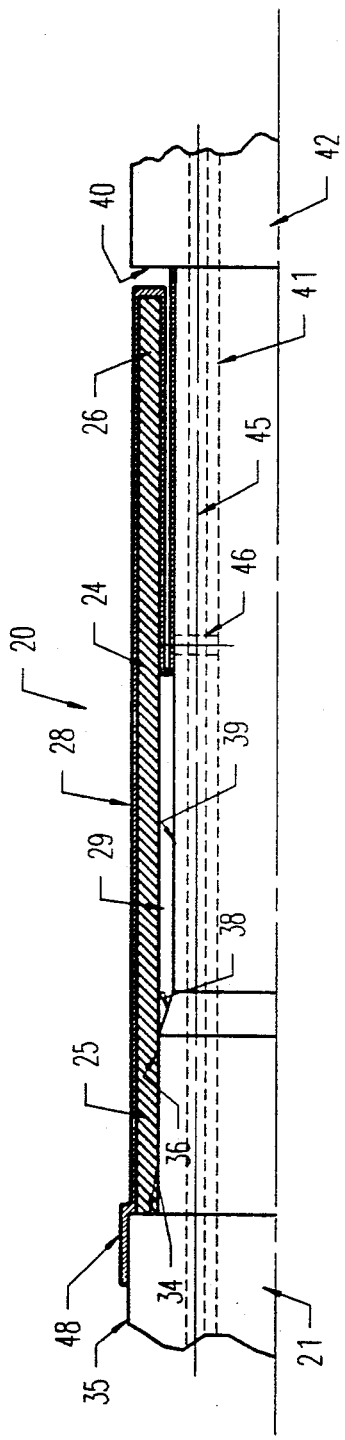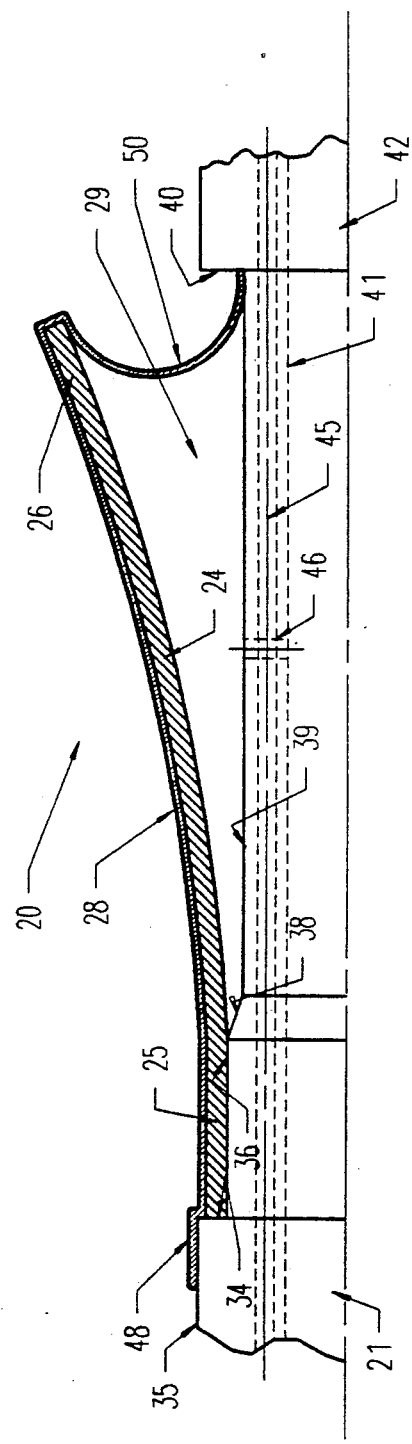

EMBOLECTOMY CATHETER, AND METHOD OF OPERATING SAME

TECHNICAL FIELD

The present invention relates generally to the field of balloon-type catheters, and, more particularly, to an improved balloon-type catheter having a concave annular recess, when inflated, for particular use in performing an embolectomy.

BACKGROUND ART

Balloon-type catheters are well known. Basically, these devices have an elongated wire-like catheter provided with a distal end adapted to be inserted into a patient's blood vessel, and provided with a proximal end adapted to remain outside the patient's body. An inflatable balloon is typically mounted on the distal marginal end portion of the catheter. Hence, the surgeon will make an incision in a blood vessel; insert the catheter, with its balloon deflated, through the incision into the blood vessel; and feed the catheter along the blood vessel to a desired position relative thereto. This position may be determined by conventional fluoroscopic techniques.

Once in position, the balloon may be selectively inflated, and the catheter may, if desired, be moved longitudinally relative to the blood vessel to perform some desired procedure. In some cases, however, the balloon is simply inflated, without any longitudinal movement relative to the blood vessel, so as to deform plaque outwardly, thereby to increase the size of a constriction within the blood vessel. This procedure is commonly known as angioplasty.

In other situations, the catheter is moved relative to the blood vessel with the balloon inflated. For example, to remove an embolus, such as a blood clot, the conventional balloon catheter is commonly passed through the embolus with its balloon deflated. Thereafter, the balloon is selectively inflated, and the proximal end of the catheter is pulled from outside the body in an attempt to physically remove the embolus from the blood vessel.

However, with such prior art techniques, the catheter is commonly inflated to a pressure substantially above the patient's systolic blood pressure in order to sufficiently stiffen the balloon to an extent necessary to dislodge an embolus when moved longitudinally relative to the blood vessel. Thus, the inflated balloon typically bears forcibly against the blood vessel. This condition may weaken the wall of the blood vessel, and tend to promote an aneurysmic condition. At the same time, such conventional catheters commonly inflate the balloon to a toroidal shape, and do not have any cavity or recess for receiving portions, if not all, of the separated embolus. Even when inflated, the toroidal shape of prior art catheters has a tendency to roll or deform to a teardrop shape when the inflated balloon frictionally engages the wall of the blood vessel and/or the embolus.

Accordingly, there is believed to be a need for an improved balloon-type catheter for use in performing an embolectomy, which catheter may be inflated to a particular shape having a concave annular recess arranged to face toward, and receive portions of, the separated embolus. At the same time, there is believed to be a further need for a particular type of balloon catheter which need not necessarily be overinflated so as to bear forcibly against the walls of the blood vessel. It is further perceived that such an improved catheter would have the advantage of reducing damage to the endothelial layer of the blood vessel.

DISCLOSURE OF THE INVENTION

The present invention provides an improved inflatable balloon-type catheter which is particularly suited for use in, but not limited to, performing an embolectomy, such as removal of a blood clot from a patient's blood vessel.

The improved apparatus broadly includes: an elongated catheter having a distal end adapted to be inserted into a patient's blood vessel, and having a proximal end adapted to remain outside the patient's body; a plurality of fingers having first ends mounted on a distal marginal end portion of the catheter in circumferentially-spaced relation to one another, these fingers having respective second ends arranged farther from the catheter distal end than the finger first ends, each of the fingers being configured as a leaf spring and having an unbiased radius of curvature such that the finger second ends will normally be spaced farther radially outwardly from the catheter than the first ends; a sleeve-like balloon surrounding the fingers and operatively secured to the catheter to define an annular inflatable chamber therebetween, the fingers being arranged within this chamber; and pressure control means for selectively varying the absolute pressure within this chamber so as to concomitantly vary the pressure differential across the balloon wall; whereby the pressure control means may be operated so as to create one pressure differential across the balloon to cause the finger second ends to move radially outwardly toward the catheter, and may be alternatively operated to create another pressure differential across the balloon to permit the fingers to move radially away from the catheter.

In use, the improved apparatus performs a novel method of removing an embolus from the blood vessel of a patient. In one aspect, this improved method broadly includes the steps of: making an incision in a blood vessel; inserting the distal end of an elongated catheter into the blood vessel through the incision, the catheter having a plurality of fingers mounted on a distal marginal end portion of the catheter in circumferentially-spaced relation to one another, the fingers having respective second ends arranged farther from the catheter distal end than the first ends, each of the fingers being configured as a leaf spring and having an unbiased radius of curvature such that the finger second ends will normally be spaced farther radially outwardly from the catheter than the finger first ends, the catheter also having a balloon surrounding the fingers and operatively secured to the catheter so as to define an inflatable chamber in which the fingers are arranged; reducing the absolute pressure within the chamber so that the pressure differential across the balloon wall will cause the finger second ends to move radially toward the catheter; passing the catheter, with its balloon deflated through an embolus-to-be-removed; increasing the absolute pressure within the chamber to permit the finger second ends to move away from the catheter; pulling the catheter proximal end, with the balloon inflated, so as to separate the embolus from the blood vessel; removing the catheter and the embolus from the blood vessel; and closing the incision.

In another aspect, the improved method includes the steps of: making an incision in a blood vessel; inserting the distal end of an inflatable balloon-type catheter into the blood vessel through the incision; passing the distal end of the catheter and the deflated balloon through an embolus-to-be-removed; increasing the absolute pressure within the balloon so as to form a cup-shaped annular recess facing toward the embolus; pulling the proximal end of the catheter so as to separate the embolus from the blood vessel; receiving at least a portion of the separated embolus in the cup-shaped recess; withdrawing the catheter and separated embolus from the blood vessel; and closing the incision.

Accordingly, the general object of this invention is to provide an improved balloon-type inflatable catheter for use in performing an embolectomy.

Another object is to provide an improved method of operating an inflatable balloon-type catheter so as to perform an embolectomy.

Another object is to provide an improved balloon-type catheter having a specially-shaped balloon which, when inflated, has an annular concave recess arranged to receive portions of the separated embolus.

Still another object is to provide an improved balloon-type catheter which need not be inflated to such an extent as to damage the endothelial layer of the blood vessel, or to promote formation of an aneurysmic condition in the blood vessel, and which is relatively stiff or rigid in a longitudinal direction, as when the proximal end is pulled, to separate the embolus from the blood vessel.

These and other objects and advantages will become apparent from the foregoing and ongoing written specification, the drawings, and the appended claims.

BRIEF DESCRIPTION OF THE DRAWINGS

FIG. 1 is a fragmentary longitudinal side elevational view of the improved catheter, this view showing the balloon as being in its deflated condition.

FIG. 2 is a fragmentary transverse vertical sectional view thereof, taken generally on line 2—2 of FIG. 1.

FIG. 3 is a fragmentary longitudinal side elevational view similar to FIG. 1, but with the balloon removed so as to show the positions of the fingers when the balloon is deflated.

FIG. 4 is a fragmentary transverse vertical sectional view, taken generally on line 4—4 of FIG. 3.

FIG. 5 is a fragmentary longitudinal side elevational view of the improved catheter shown in FIG. 1, but depicting the balloon as having been inflated.

FIG. 6 is a fragmentary transverse vertical sectional view thereof, taken on line 6—6 of FIG. 5.

FIG. 7 is a fragmentary longitudinal side elevational view similar to FIG. 5, but showing the balloon as having been removed to show the positions of the fingers after the balloon has been inflated.

FIG. 8 is a fragmentary transverse vertical sectional view, taken generally on line 8—8 of FIG. 7.

FIG. 9 is an enlarged fragmentary longitudinal horizontal sectional view, taken generally on line 9—9 of FIG. 1, showing the deflated position of one finger.

FIG. 10 is a fragmentary enlarged longitudinal horizontal sectional view, taken generally on line 10—10 of FIG. 5, showing the inflated position of the corresponding finger shown in FIG. 9.

DESCRIPTION OF THE PREFERRED EMBODIMENT(S)

Figure 11:
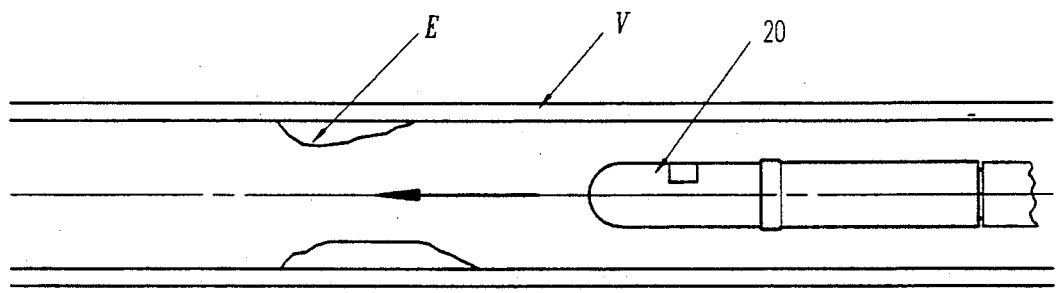
FIG. 11 is a view showing the improved catheter inserted into a blood vessel with the balloon deflated.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Referring now to the drawings, this invention, in one aspect, provides an improved inflatable balloon-type catheter, of which a presently-preferred embodiment is generally indicated at 20.

The improved catheter is shown as broadly including an elongated catheter, generally indicated at 21, having a leftward rounded spherical distal end 22 adapted to be inserted into a blood vessel (either venous or arterial), as described infra, and having a rightward proximal end 23 adapted to remain outside the patient's body. The improved catheter further includes a plurality (i.e., two or more) of fingers, severally indicated at 24, having leftward first marginal end portions 25 mounted on the catheter and having rightward second marginal end portions 26 arranged to move radially toward and away from the catheter. As best shown in FIGS. 9 and 10, a balloon 28 is mounted on the catheter so as to define a variable-volume inflatable chamber 29 between the balloon and catheter, in which chamber the several fingers are arranged. Pressure control means, schematically indicated at 30, such as a squeeze bulb, a syringe, or some other automatic device for controlling the pressure within chamber 29, is arranged adjacent the proximal end of the catheter. A piezoelectric transducer, generally indicated at 31, is mounted on the distal marginal end portion 32 of the catheter between the distal end 22 thereof and finger first ends 25, and is arranged to supply an electrical signal indicative of the pressure or velocity of blood proximate the transducer to a sensor 33 located adjacent the proximal end of the catheter.

As best shown in FIGS. 1, 3, 5, 7, 9 and 10, catheter 21 is a greatly-elongated tubular member provided with an annular recess in its distal marginal end portion. As best shown in FIGS. 9 and 10, this recess is bounded a rightwardly-facing annular vertical surface 34 extending inwardly from the outer cylindrical surface 35 of the catheter, a outwardly-facing polygonal surface 36 extending rightwardly therefrom, a rightwardly- and outwardly-facing frusto-conical surface 38, an outwardly-facing horizontal cylindrical surface 39, and a leftwardly-facing annular vertical surface 40 extending outwardly therefrom to rejoin catheter outer cylindrical surface 35.

A longitudinally-extending blind hole 41 extends into the catheter from its proximal end 23 and bottoms immediately adjacent the distal nose of the catheter, to receive and accommodate a wire stylet 42. Stylet 42 may be selectively inserted into the catheter to stiffen it such that the catheter may be longitudinally fed into a blood vessel from outside the patient's body. Piezoelectric transducer 31 is shown as being mounted on the distal marginal end portion of the catheter between distal end face 22 and the recess, and conductors 43, 44 are shown as passing through suitable lumens, one of which is indicated at 45 in FIGS. 9 and 10, respectively, provided in the catheter. Transducer 31 is arranged to sense either the pressure or velocity of blood approximate the distal marginal end portion of the catheter, and is arranged to supply an electrical signal indicative of such sensed pressure or velocity via conductors 43, 44 to a pressure or velocity sensor 33. Thus, the catheter is a much-elongated flexible whip-like member, which may be inserted longitudinally into a blood vessel and moved longitudinally there-along by manipulation from without the body, to a desired position. Radial hole 46 communicates stylet hole 41 with recess surface 39.

As best shown in FIGS. 9 and 10, the balloon 28 is an open-ended tubular member formed of a suitable elastomeric material, such as silastic. The left marginal end portion 48 of the balloon surrounds, and is suitably secured in a fluid-tight manner, to catheter outer surface 35 between the recess and distal end 22. The right marginal end portion 49 of the balloon surrounds, and is suitably secured again in a fluid-tight manner, to catheter recess surface 39 immediately adjacent recess end wall 40. Thus, the balloon defines with the catheter the variable-volume chamber 29 therebetween, which chamber communicates with the pressure control means 30 via connecting passageways 46,41. If desired, the stylet may be removed after the catheter has been inserted past a particular clot-to-be-removed, in order to increase the cross-sectional area of hole 41. Alternatively, the stylet can possibly remain in place, with the annular space between stylet 42 and hole 41 providing the passageway communicating via radial hole 46 with chamber 29.

Still referring principally to FIGS. 9 and 10, each finger is shown as being an elongated bar-like member having a substantially-rectangular transverse cross-section. The leftward or first marginal end portions 25 of these fingers are secured, as by adhesive bonding or the like, to the several faces of polygonal surface 36. In the illustrated embodiment, polygonal surface 36 is octagonal, and there are eight such fingers. However, persons skilled in this art will readily appreciate that polygonal surface 36 could be provided with a greater or lesser number of such faces. Indeed, surface 36 need not be polygonal, but may be arcuate is desired. In this event, the left marginal end portions of the fingers would be appropriately configured so as to complimentarily engage this arcuate surface.

Each finger is configured as a leaf-spring, and has an unbiased arcuate shape, shown in FIG. 10, generated about a radius of curvature. In other words, each finger is normally a curved or arcuate member, and is mounted on the catheter such that the second ends 26 thereof will normally be spaced farther away from the catheter than the first marginal ends 25. As previously noted, the several fingers 24, of which eight are shown in the preferred embodiment, are operatively arranged within chamber 29. When the pressure control means 30 is operated so as to evacuate the chamber, the external pressure acting on the outer surface of the balloon will be sufficient to urge the fingers to bend or flex to a horizontally-elongated substantially-straight position, as shown in FIG. 9, in which such fingers are operatively arranged within the catheter recess.

The pressure control means 30 may be operated alternatively to vary the absolute pressure within the chamber 29. If the pressure within chamber 29 is permitted to equalize with the ambient pressure, then the springs will slowly move substantially to their unbiased shape, as shown in FIG. 10. If desired, the pressure control means could be operated so as to pressurize chamber 29 positively relative to the ambient pressure, to cause the fingers to bend or curl outwardly even further.

Still referring to FIGS. 9 and 10, it will be noted that when the fingers are moved to their outwardly-extended (i.e., undeformed) positions, as shown in FIG. 10, the fingers act like stiffening splines to impart some rigidity to the inflatable chamber when the inflated catheter is pulled rearwardly (i.e., toward to proximal end) to dislodge an embolus. Thus, the inflatable balloon is relatively stiff in the longitudinal direction, but relatively flexible in a radial direction. In other words, the improved device may have sufficient stiffness in a longitudinal direction to dislodge an embolus from a blood vessel, without exerting undue pressure in a radial direction that would tend to promote an aneurysmic condition.

The operation of the improved catheter is graphically shown in FIGS. 11–14. Referring first to FIG. 11, the surgeon first makes an appropriate incision in the patient's blood vessel V, or some other vessel commensurating therewith. Thereafter, the surgeon progressively feeds the catheter into the patient's blood vessel V until the distal end is in an appropriate and desired position. This may be determined by conventional fluoroscopic techniques. Thus, FIG. 11 depicts the catheter, with its balloon deflated, as having been inserted into, and moved longitudinally along, the patient's blood vessel V so as to be aligned just below an embolism E.

Figure 12:
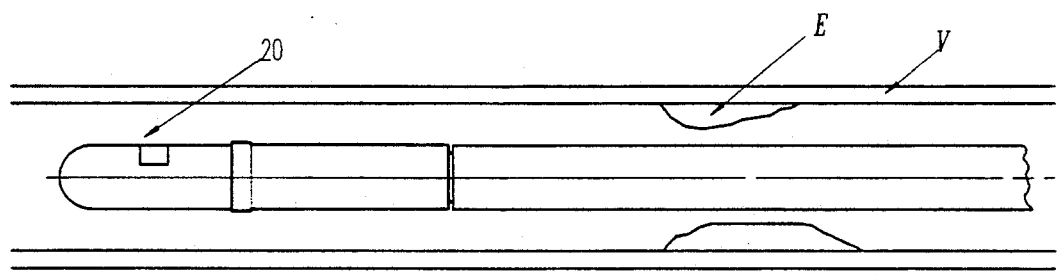
FIG. 12 is a view similar to FIG. 11, but showing the catheter, with the balloon still deflated, as having been pushed forwardly and passed through an embolism-to-be-removed.

Thereafter, the distal marginal end portion of the catheter, with its balloon still deflated, is pushed through the embolism, as graphically illustrated in FIG. 12.

Figure 13:
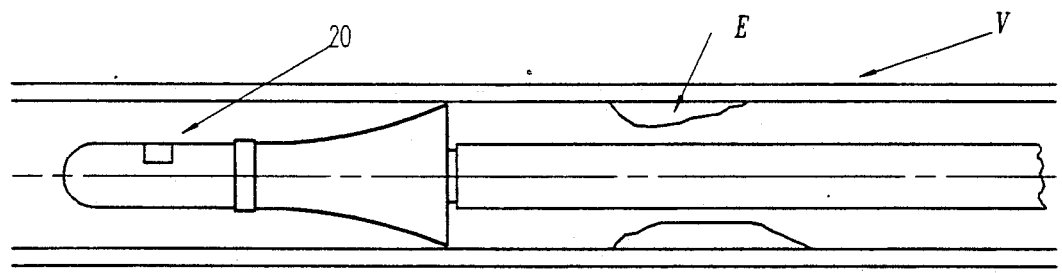
FIG. 13 is a view similar to FIG. 12, but showing the balloon as having been inflated.

Once in this position, the pressure control means is operated to suitable inflate chamber 29, thereby causing the fingers to curl outwardly. As shown in FIGS. 10 and 13, the inflated balloon will have a concave annular recess, generally indicated at 50, facing rearwardly toward the proximal end of the catheter and toward the embolus E.

Figure 14:
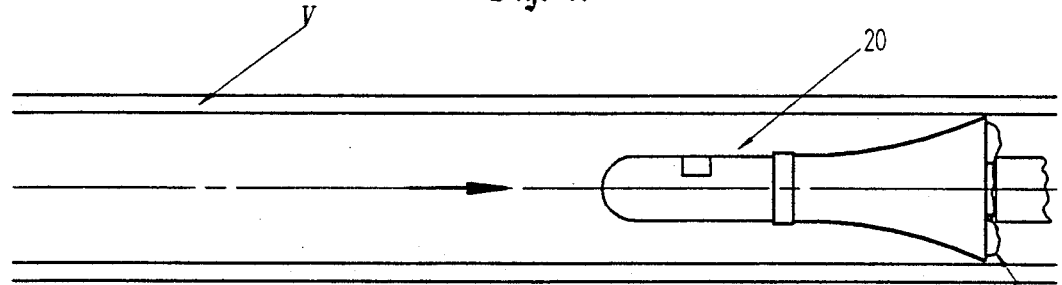
FIG. 14 is a view similar to FIG. 13, but showing the proximal end of the catheter as having been pulled rearwardly so as to separate the embolism from the blood vessel, with the separated embolus being received in the recess provided in the shaped balloon.

Thereafter, the surgeon pulls the proximal end of the catheter, as shown in FIG. 14, to physically cause the embolus E to separate from the wall of the blood vessel V. The separated portions of the embolus are conveniently received within the annular balloon recess.

Thereafter, the surgeon withdraws the catheter and the embolus from the patient's body, and closes the incision.

Therefore, in summary, the improved apparatus comprises an inflatable balloon-type catheter, which is relatively stiff in a longitudinal direction, by virtue of stiffening the stiffening fingers 24, when pulled rearwardly, but which need not be over-inflated so as to promote an aneurysmic condition, and which functions to readily dislodge an embolus from the inside wall of a blood vessel. At the same time, the balloon of the improved catheter does not have a tendency to deform or roll as the catheter is pulled rearwardly to separate the embolus.

MODIFICATIONS

The present invention contemplates that many changes and modification may be made. For example, the balloon may take many forms, and may be formed of many different materials. The number of fingers may be changed or varied, as desired. In addition, if desired, other means might be provided to splay the rearward ends of the fingers. Indeed, in some cases, the fingers may be omitted entirely in favor of some other means for inflating the balloon to the shape having a rearwardly-facing concave annular recess.

The piezoelectric pressure or velocity sensor, while presently preferred, is optional, and may be omitted if desired. The pressure control means may be a squeeze bulb, a syringe, or some means for automatically varying and regulating the pressure within the chamber. For example, once inserted into the patient's blood vessel, the patient's blood pressure will vary between its diastolic and systolic limits. The pressure control means may be operated so as to match the patient's varying pressure, so that the relative pressure differential, if any, across the walls of the balloon will remain substantially constant at all times.

A unique feature of the invention is that the portion of the balloon immediately about the concave recess 50, will progressively "walk" forwardly beneath the fingers as they are moved from their outwardly-extended to their inwardly-retracted positions, as comparatively illustrated in FIGS. 9 and 10. Thus, even a small pressure differential across the balloon will cause the balloon to move to a folded-flat condition when the fingers are fully-retracted, as graphically shown in FIG. 9.

The dimensions, sizes, materials of construction, and the like, are not deemed critical and may be readily varied by persons skilled in this art. Thus, the length and/or number of the fingers may be readily varied, as desired. While it is presently preferred that the fingers be mounted within an annular recess extending into the catheter, so that such fingers do not extend outwardly beyond the transverse profile of the catheter when the fingers are in their deflated condition, this arrangement is not invariable. Other types of springs may be substituted for those shown.

Therefore, while a presently-preferred embodiment of the improved embolectomy catheter has been shown and described, and several modifications thereof discussed, persons skilled in this art will readily appreciate that various additional changes and modifications may be made without departing from the spirit of the invention, as defined and differentiated by the following claims.

What is claimed is:

1. An inflatable balloon-type catheter for use in performing an embolectomy, comprising:

an elongated catheter having a distal end adapted to be inserted into a patient's blood vessel, and having a proximal end adapted to remain outside the patient's body;

a plurality of fingers having first ends mounted on a distal marginal end portion of said catheter in circumferentially-spaced relation to one another, said fingers having respective second ends arranged farther from said catheter distal end than said finger first ends, each of said fingers being configured as a leaf-spring and having an unbiased radius of curvature such that said finger second ends will normally be spaced farther radially outwardly from said catheter than said first ends;

a balloon surrounding said fingers and operatively secured to said catheter so that said fingers are arranged within an inflatable chamber defined between said catheter and said balloon; and pressure control means in communication with the inflatable chamber for selectively varying the absolute pressure within said chamber so as to concomitantly vary the pressure differential across said balloon;

whereby said pressure control means may be operated so as to create one pressure differential across said balloon to cause said finger second ends to move radially toward said catheter, and another pressure differential across said balloon to cause said fingers to move radially away from said catheter.

2. An inflatable balloon-type catheter as set forth in claim 1 wherein said catheter is provided with an annular recess in its distal marginal end portion, and wherein said finger first ends are arranged in said recess.

3. An inflatable balloon-type catheter as set forth in claim 2 wherein said finger second ends are arranged in said recess when said pressure control means is operated to create said one pressure differential across said balloon.

4. An inflatable balloon-type catheter as set forth in claim 2 wherein a portion of said recess is bounded by a polygonal surface.

5. An inflatable balloon-type catheter as set forth in claim 1 wherein each of said fingers has a substantially-rectangular transverse cross-section.

6. An inflatable balloon-type catheter as set forth in claim 1 wherein the transverse cross-section of each finger does not vary substantially between its first and second ends.

7. An inflatable balloon-type catheter as set forth in claim 1 wherein said finger first marginal end portions are adhesively bonded to said catheter.

8. An inflatable balloon-type catheter as set forth in claim 1 wherein the portion of said balloon between said finger second ends and said catheter is bowed to an arcuate shape arranged radially inwardly of said finger second ends when the absolute pressure within said chamber is less than the pressure within said blood vessel.

9. An inflatable balloon-type catheter as set forth in claim 1, and further comprising a transducer mounted on said distal marginal end portion for measuring a parameter of blood.

10. The method of removing an embolism from a blood vessel of a patient, comprising the steps of:

making an incision in said blood vessel;

inserting the distal end of a catheter into said blood vessel through said incision, said catheter having a plurality of fingers mounted on the distal marginal end portion of said catheter in circumferentially-spaced relation to one another, said fingers having respective second ends arranged farther from said distal end than said first ends, each of said fingers being configured as a leaf-spring and having an unbiased radius of curvature such that said finger second ends will normally be spaced farther from said catheter than said finger first ends, said catheter also having a balloon surrounding said fingers and operatively secured to said catheter so as to define an inflatable chamber between said balloon and catheter in which said fingers are arranged;

reducing the absolute pressure within said chamber such that the pressure differential across said balloon will cause said finger second ends to move radially toward said catheter;

passing said catheter with such deflated balloon through an embolism-to-be-removed;

increasing the absolute pressure within said chamber to permit said finger second ends to move away from said catheter;

pulling the proximal end of said catheter with such inflated balloon so as to remove said embolism;

removing said catheter and separated embolism from said blood vessel; and closing said incision.

11. The method as set forth in claim 10 wherein said balloon is inflated by increasing the pressure within said chamber so that the pressure differential across said balloon is substantially zero and so that said fingers may move toward their unbiased arcuate shapes.

12. The method as set forth in claim 10, and further comprising the additional step of:

forming a cup-shaped annular recess in said balloon after the pressure in said chamber has been increased to receive portions of the separated embolism.

13. The method as set forth in claim 10 and further comprising the additional step of measuring a parameter of blood in said blood vessel.

14. The method of removing an embolism from the blood vessel of a patient, comprising the steps of:

making an incision in said blood vessel;

inserting the distal end of an inflatable balloon-type catheter into said blood vessel through said incision;

passing the distal end of said catheter and the deflated balloon through an embolism;

inflating said balloon so as to form a cup-shaped annular recess facing toward said embolism;

pulling the proximal end of said catheter so as to separate said embolism from said blood vessel;

receiving a portion of such separated embolism in said annular recess;

withdrawing said embolism and catheter from said blood vessel; and closing said incision.

15. The method as set forth in claim 14 wherein said balloon is inflated to a pressure such that said balloon will not substantially damage the endothelial layer of said blood vessel.

16. The method as set forth in claim 14 and further comprising the additional step of measuring a parameter of blood in said blood vessel.

* * * * *